US007066901B2

(12) United States Patent
Kuth et al.

(10) Patent No.: US 7,066,901 B2
(45) Date of Patent: Jun. 27, 2006

(54) MR-COMPATIBLE FLUID VALVE

(75) Inventors: Rainer Kuth, Herzogenaurach (DE); Thomas Rupprecht, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 373 days.

(21) Appl. No.: 10/126,045

(22) Filed: Apr. 19, 2002

(65) Prior Publication Data
US 2002/0183680 A1 Dec. 5, 2002

(30) Foreign Application Priority Data
Apr. 20, 2001 (DE) ................................ 101 19 452

(51) Int. Cl.
*A61M 5/00* (2006.01)
(52) U.S. Cl. .................... 604/9; 604/7; 604/8; 604/247
(58) Field of Classification Search ............. 604/7–10, 604/6.16, 6.1, 247, 30–32, 65–67; 623/23.64, 623/23.68; 251/157, 159, 160, 161, 12, 58, 251/89, 93, 101, 187, 192, 208; 137/251.1, 137/384.2, 384.8
See application file for complete search history.

(56) References Cited

U.S. PATENT DOCUMENTS

| 3,595,240 | A |   | 7/1971  | Mishler |
|-----------|---|---|---------|---------|
| 4,551,128 | A | * | 11/1985 | Hakim et al. .................. 604/9 |
| 4,781,673 | A | * | 11/1988 | Watanabe ...................... 604/9 |
| 4,784,660 | A | * | 11/1988 | Fischell .................. 623/23.66 |
| 5,167,615 | A | * | 12/1992 | East et al. ..................... 604/9 |
| 5,637,083 | A | * | 6/1997  | Bertrand et al. ............... 604/9 |
| 5,643,194 | A | * | 7/1997  | Negre ........................... 604/8 |
| 6,697,662 | B1 | * | 2/2004 | Sawitowski et al. ........ 600/414 |

FOREIGN PATENT DOCUMENTS

| EP | 0 233 325 | 8/1987 |
|----|-----------|--------|
| GB | 2 143 008 | 1/1985 |

* cited by examiner

Primary Examiner—Tatyana Zalukaeva
Assistant Examiner—Leslie R. Deak
(74) Attorney, Agent, or Firm—Schiff Hardin LLP

(57) ABSTRACT

An implantable fluid valve for the adjustable limitation of the fluid pressure in the brain of a patient, has all valve component parts composed of non-magnetic material, thereby making the valve MR-compatible.

9 Claims, 1 Drawing Sheet

MR-COMPATIBLE FLUID VALVE

BACKGROUND OF THE INVENTION

1. Field of the Invention

The present invention is directed to an implantable fluid valve for the adjustable limitation of the fluid pressure in the brain of a patient.

2. Description of the Prior Art

Valves that allow a setting of the maximum pressure from the outside of a patient, and automatically allow fluid to flow off given excess pressure, are required for patients whose discharge of fluid from the brain is abnormal.

Valves that can be set from the outside by means of magnetic forces are commercially available. These valves are not MR-compatible. (As used herein, MR stands for magnetic resonance.) Examination of the patient in conventional MR scanners thus is not possible without risk, particularly given flux densities of 1 T and above. A maladjustment of the programmed pressure level or even damage to the implanted valves is a frequent complication even given the use of low-field MR scanners.

Although having parts composed of rubber, a setting of the fluid pressure is not possible at all with a fluid valve disclosed by U.S. Pat. No. 3,595,240, which derives from a time when magnetic resonance systems were not yet known, so that the problem of an MR-compatible fluid valve did not arise at all.

In one embodiment of a cerebrospinal fluid shunt valve disclosed in U.S. Pat. No. 4,551,128, adjustment is possible by only puncturing the scalp to allow access of a screwdriver or the like to an adjustment screw. This is unacceptable in practice particularly because of the risk of infection and moreover this fluid valve has metallic parts that are fundamentally incompatible with MR. In another embodiment of this known valve, magnetic adjustment for the adjustable limitation of the fluid pressure is even worse as to MR compatibility. That embodiment includes magnetic component parts that could create life-threatening complications in conjunction with the extremely high field strengths of the basic magnetic field of an MR system. Thus, this known fluid valve is neither suitable for utilization with MR monitoring observation nor was this even envisioned.

The same is also true of a fluid valve according to U.S. Pat. No. 5,167,615 that likewise contains magnets for setting the respective pressure.

British patent application GB 2 143 008 as well as European patent application 0 233 325 also disclose valves that are not MR-compatible. The use of stainless steel is expressly prescribed in the former which makes this valve non-MR-compatible because MR compatibility not only involves avoiding magnetic components but also avoiding components having good electrical conductivity since considerable artifacts could otherwise arise.

SUMMARY OF THE INVENTION

An object of the present invention is to provide an adjustable MR-compatible fluid valve.

This object is inventively in an adjustable valve wherein all valve parts are composed of MR-compatible non-magnetic material. A push-button mechanism with key stems that are sub-cutaneously actuatable through the scalp can be provided for setting the valve parts that can be rotated relative to one another.

As a result of the inventive fabrication of all valve components of non-magnetic material, for example aluminum, brass, titanium, V4A steel (CrNiMo steel), plastic or combinations of these materials, a fluid valve is achieved that enables MR examinations of the patient after the implantation. It has been shown that it is precisely those patients who have a discharge disorder who require MR examinations of the head with above-average frequency. The need for MR-compatibility of the fluid valve is thus intensified. The pushbutton mechanism for the rotary adjustment of the valve parts relative to one another can be constructed similar to the rotary mechanism of ballpoint pens, automatic pencils or the like wherein a rotary motion is triggered when a button is pressed. Two pushbuttons are preferably provided for the inventive adjustment of the setting parts of a fluid valve, one opening the valve step-by-step and the other pushbutton producing a step-by-step closing of the valve.

In a further embodiment of the invention, an interlock mechanism having an unlocking element can be provided that must be actuated simultaneously with the setting elements. An adjustment of the fluid valve by actuating the pushbutton mechanism can occur only when the unlocking element, i.e., for example, a further enable button, also is pressed. This prevents an inadvertent adjustment of the pressure setting of this fluid valve when the region of the head of the patient where the fluid valve is implanted under the scalp is inadvertently struck or touched, which could possibly lead to serious health risks.

Markings that are visible using imaging diagnostic systems can be provided at the valve parts that are adjustable relative to one another, for example oblong hollow members filled with an MR-visible fluid. Reference markers are also possible that can be seen in X-ray images, ultrasound images or the like.

DESCRIPTION OF THE PREFERRED EMBODIMENTS

Figure 1:
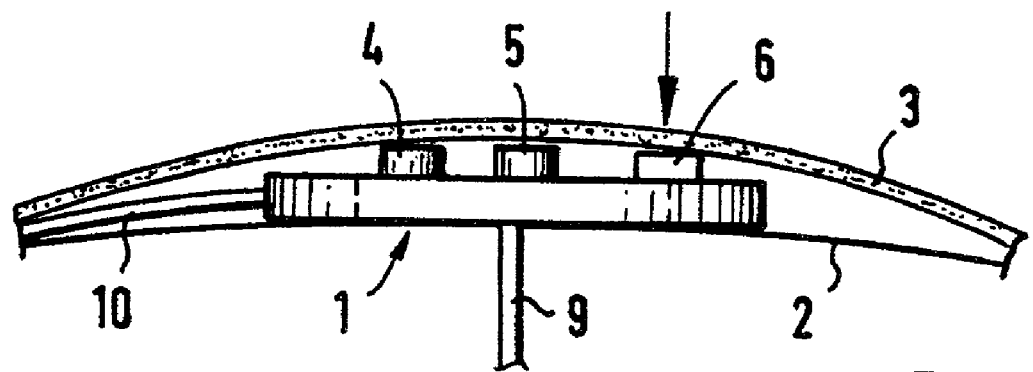
FIG. 1 is a schematic section through the implantation location of an inventive fluid valve in the head of a patient.
Figure 2:
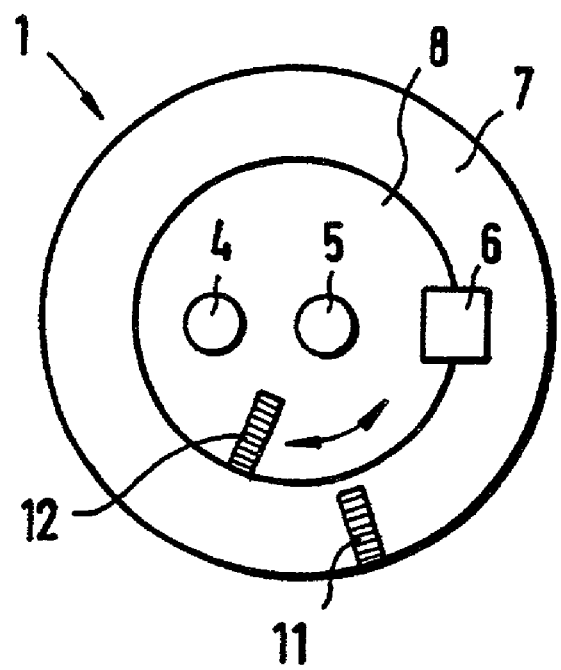
FIG. 2 is a plan view of the fluid valve in FIG. 1.

The illustrated fluid valve 1 is secured to the skull bone 2 under the scalp 3, so that the adjustment pushbuttons 4 and 5 as well as an unlocking pushbutton 6 can be actuated through the scalp 3. The unlocking pushbutton 6 serves for enabling the adjustment pushbuttons 4 and 5. The adjustment pushbuttons 4 and 5 can cause an adjustment of the valve body parts 7 and 8 that are rotatable relative to one another only when the unlocking pushbutton 6 also is pressed. The pushbuttons 4 and 5 respectively serve for opening and for closing the valve. The inner valve part 8 turns one step in the one or other direction relative to the outer part 7 each time a pushbutton 4 or 5 is pressed. Hose connection conduits 9 and 10 allow the inventive fluid valve to be inserted into the fluid system of the patient, so that a discharge of the fluid supplied to the fluid valve 1 at 9 ensues via the drain hose conduit 10.

In order to be able to recognize the setting of the fluid valve from the outside, reference markers 11 and 12 are attached to the valve parts 7 and 8 that are rotatable relative to one another. These reference markers can be visual with an imaging diagnostic system, for example an X-ray, ultrasound, or MR system or the like. For recognition in magnetic resonance examinations, these reference markers 11 and 12 can be oblong hollow members filled with an MR-visible fluid. For identifying the valve position, a slice is therefore to be examined such that both hollow members lie precisely in this slice plane. This is checked in the image by the length of the image of the hollow member in the slice image being measured. If the measured value is too small, then the measurement layer has been incorrectly placed. The adjustment of the valve, and thus the opening pressure, are linearly calculated from the angle of the hollow bodies relative to one another.

Although modifications and changes may be suggested by those skilled in the art, it is in the intention of the inventors to embody within the patent warranted hereon all changes and modifications as reasonably and properly come within the scope of their contribution to the art.

We claim:

1. An implantable fluid valve comprising:
   a plurality of valve parts including an inlet adapted to receive cerebrospinal fluid, an outlet adapted to discharge cerebrospinal fluid, adjustable components disposed in a pathway between said inlet and said outlet for adjusting fluid flow through said pathway, an extremely actuatable pushbutton mechanism, and an unlocking mechanism which interacts with said pushbutton mechanism, and which has a subcutaneously actuatable unlocking element, actuated by externally applied pressure, which must be simultaneously actuated together with actuation of said pushbutton mechanism to allow said pushbutton mechanism to adjust said adjustable components; and
   all of said plurality of valve parts being composed of an MR-compatible material.

2. A fluid valve as claimed in claim 1 wherein said pushbutton interact with said adjustable components to adjust said adjustable components in steps by repeated actuation of one of said pusbuttons while said unlocking mechanism is actuated.

3. A fluid valve as claimed in claim 1 wherein said unlocking element is an unlocking pushbutton.

4. A fluid valve as claimed in claim 1 wherein said adjustable components include first and second relatively adjustable components, and further comprising reference markers disposed on said relatively adjustable components which are visible using a diagnostic imaging system.

5. A fluid valve as claimed in claim 4 wherein said reference markers comprise hollow members filled with an MR-visible fluid.

6. A fluid valve as claimed in claim 1 wherein said MR-compatible non-magnetic metallic material is selected from the group consisting of aluminum, brass, titanium, CrNiMo steel, and combinations of aluminum, brass, titanium, and CrNiMo steel.

7. A fluid valve as claimed in claim 1 wherein all of said plurality of valve parts are composed of an MR-compatible, non-metallic material.

8. A fluid valve as claimed in claim 1 wherein said unlocking element is an unlocking pushbutton.

9. A fluid valve as claimed in claim 1 wherein said pushbuttons interact with said adjustable components to adjust said adjustable components in steps by repeated actuation of one of said pushbuttons while said unlocking mechanism is actuated.

* * * * *